United States Patent [19]

Kok

[11] 4,153,841
[45] May 8, 1979

[54] PNEUMOENCEPHALOGRAPHY CHAIR

[75] Inventor: Pieter W. Kok, Trumbull, Conn.

[73] Assignee: North American Philips Corporation, New York, N.Y.

[21] Appl. No.: 830,759

[22] Filed: Sep. 6, 1977

Related U.S. Application Data

[62] Division of Ser. No. 691,289, Jun. 1, 1976, Pat. No. 4,071,231.

[51] Int. Cl.² ................... G01N 21/00; G01N 23/00; G21K 5/06; G21K 5/08
[52] U.S. Cl. ................................ 250/439 R; 250/456
[58] Field of Search ............... 250/490, 491, 444, 447, 250/439 R, 445 R, 445 T; 269/322, 323, 325, 328

[56] References Cited

U.S. PATENT DOCUMENTS 3,655,967  4/1972  Finkenzeller et al. ........... 250/439 R

FOREIGN PATENT DOCUMENTS 2014151  12/1971  Fed. Rep. of Germany ...... 250/439 R
2348039  4/1975  Fed. Rep. of Germany ...... 250/439 R Primary Examiner—Craig E. Church
Assistant Examiner—Thomas P. O'Hare
Attorney, Agent, or Firm—Thomas A. Briody; Jack E. Haken

[57]  ABSTRACT

Chair apparatus specially adapted for detachable mounting on a tiltable tomography table to restrain and support a patient and his head for tomographic exposures during pneumoencephalography. The chair apparatus positions the patient's head close to the tomography table and permits multiaxial rotation of the patient about his head so that a defined isocenter in the patient's brain does not move with respect to the table. Two axes of rotation intersect the geometric center of tomographic study.

3 Claims, 21 Drawing Figures

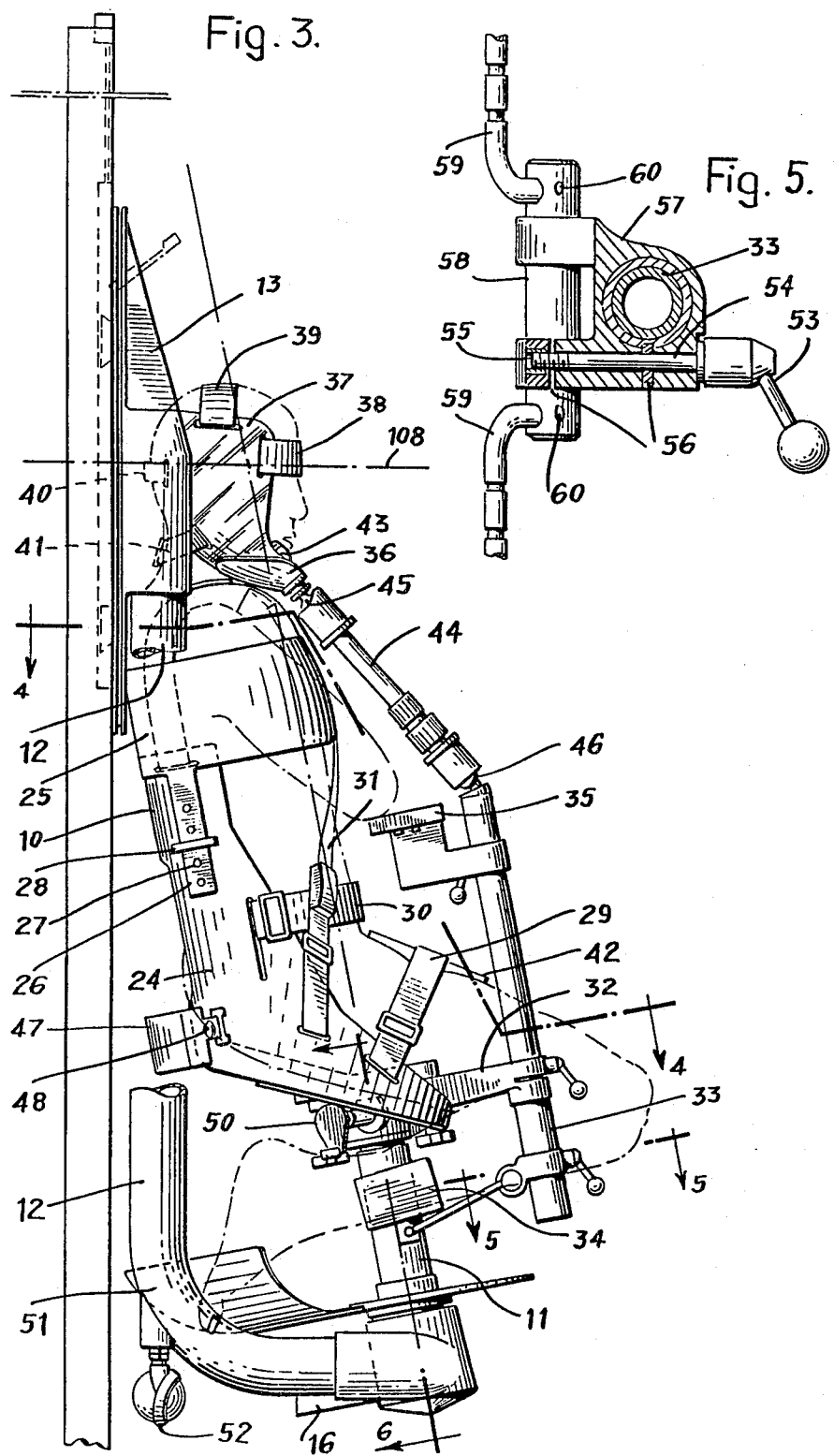

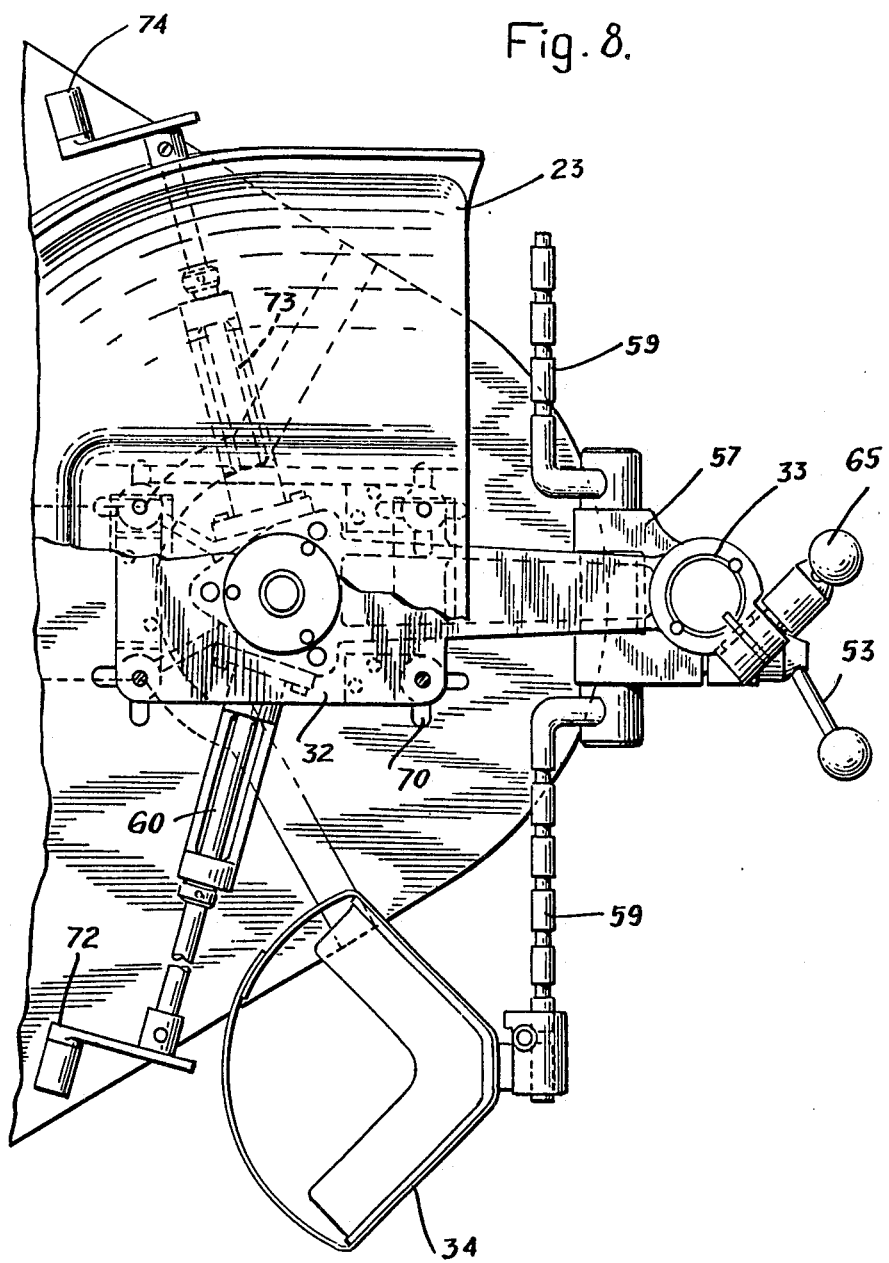

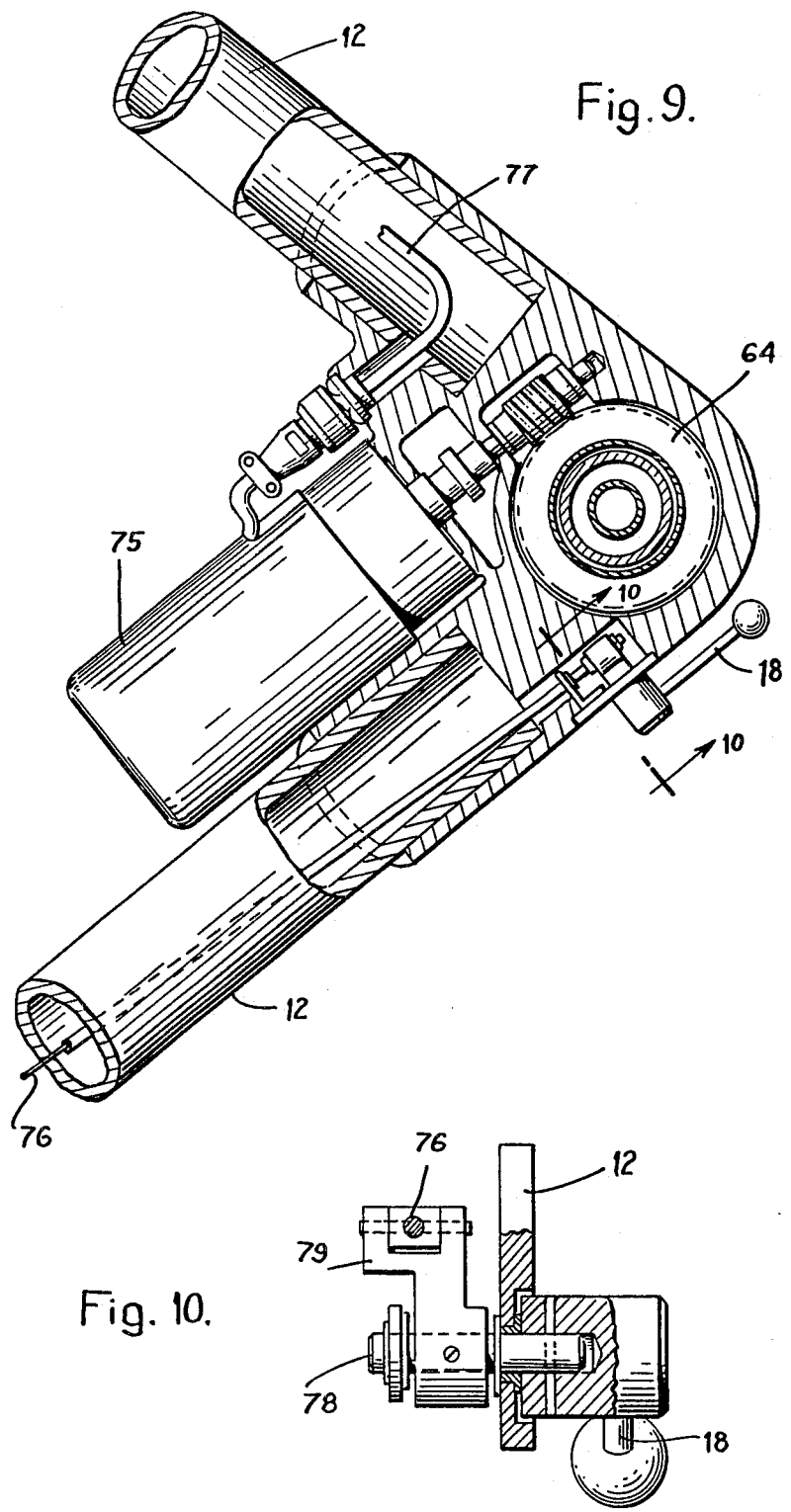

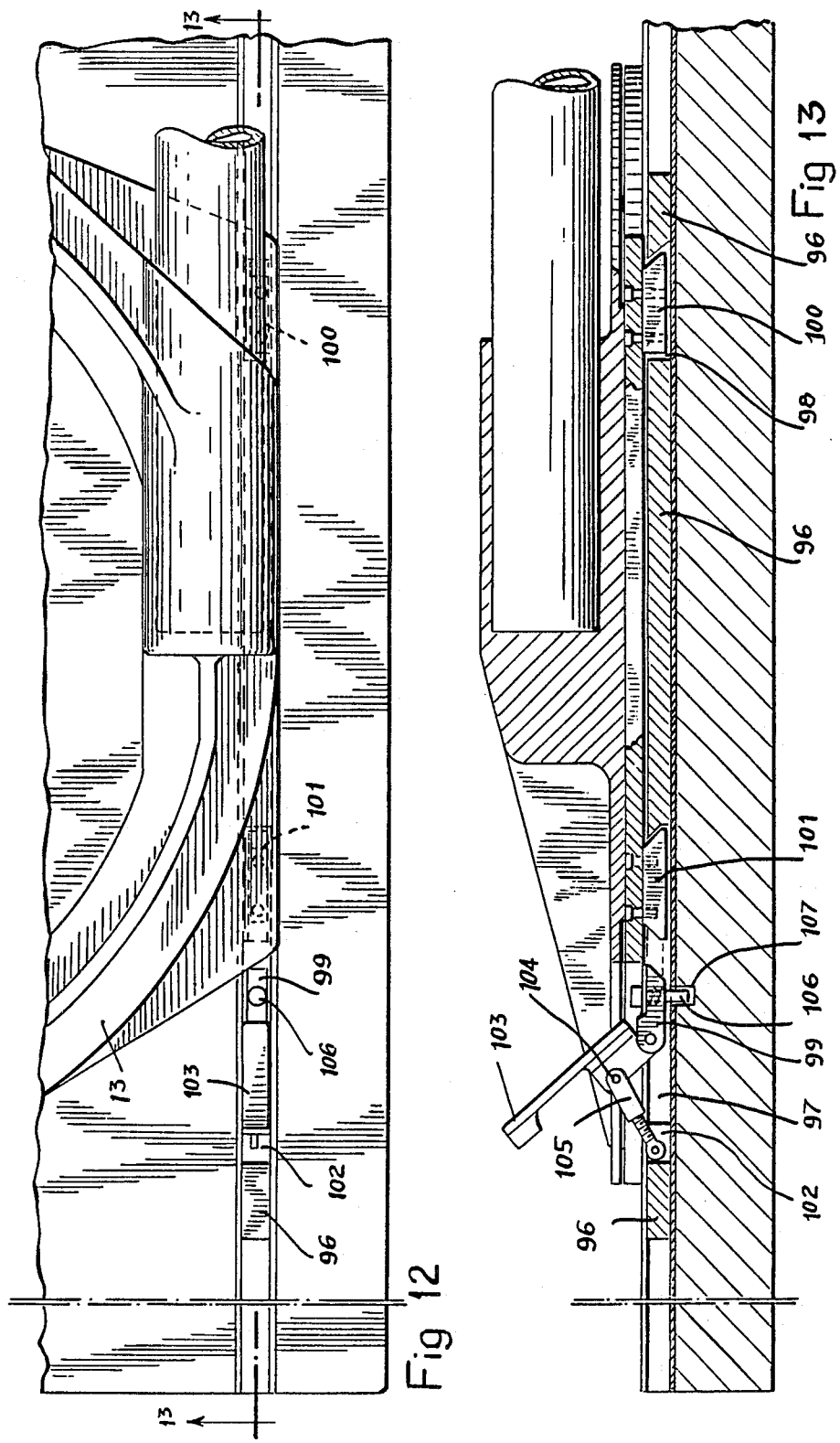

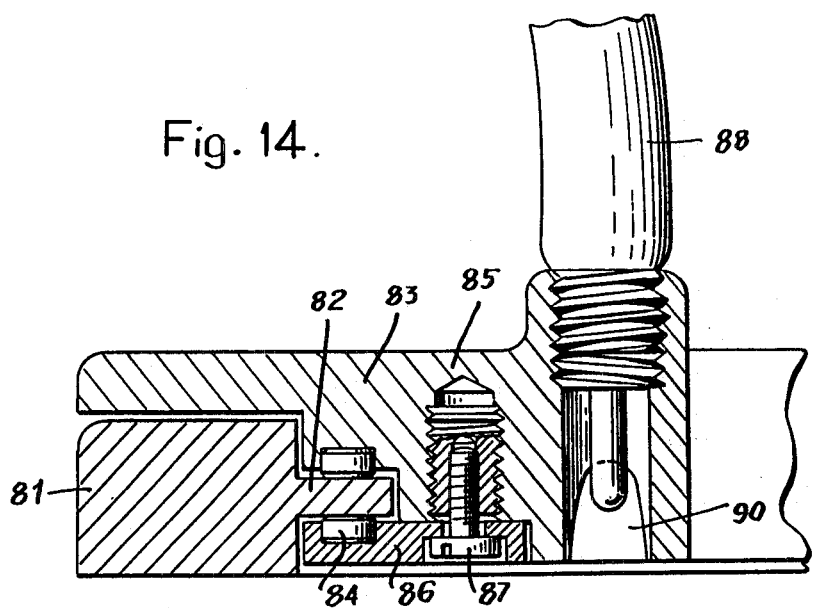
Fig. 14.
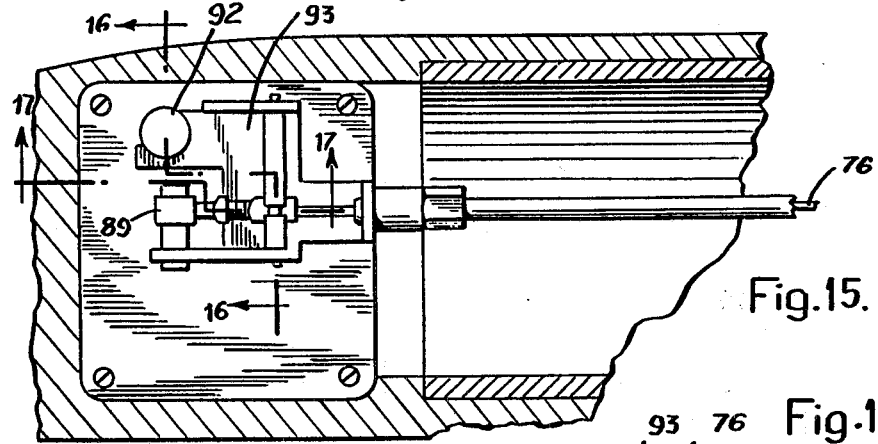
Fig. 15.
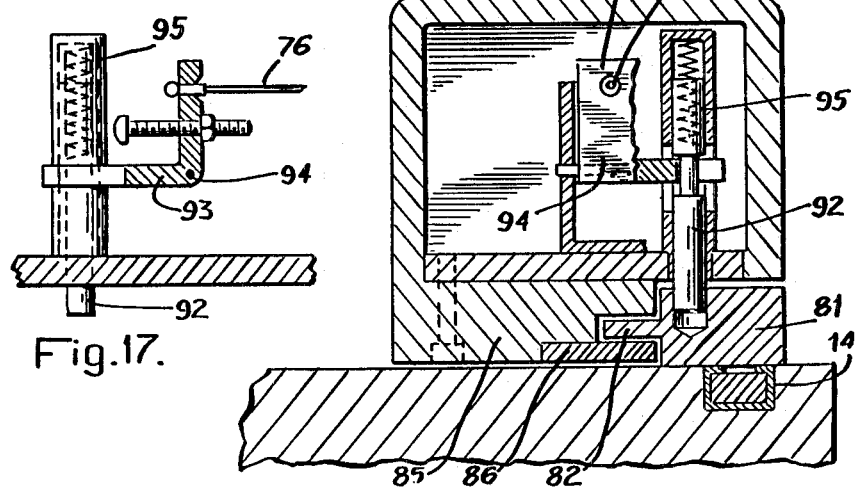
Fig. 16.
Fig. 17.

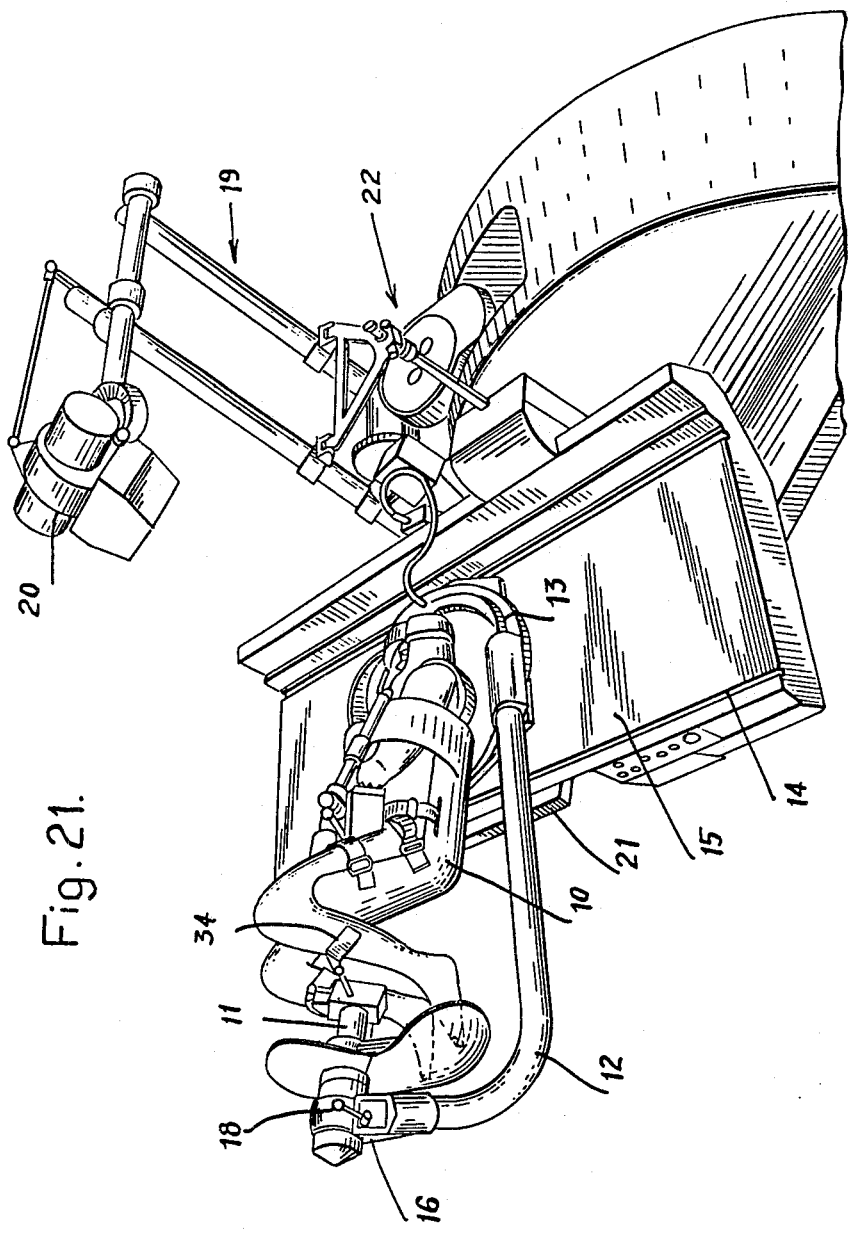

PNEUMOENCEPHALOGRAPHY CHAIR

This is a division of application Ser. No. 691,289, filed June 1, 1976 now U.S. Pat. No. 4,071,231.

BACKGROUND OF THE INVENTION

1. Field of the Invention

This invention pertains to the fields of tomography and pneumoencephalography, and more specifically to patient supporting apparatus for making tomograms during pneumoencephalography.

2. Description of the Prior Art

Pneumoencephalography is a medical procedure for determining the size and location of brain tumors. A tumor in the brain normally distorts the shape of the ventricles or cavities in the brain. Accordingly, a picture of the exact shape of the ventricles would indirectly reveal to a great extent the size and location of any major tumor. Unfortunatley the ventricles are normally filied with cerebral fluid, which absorbs x-rays about as well as brain tissue, so that the ventricles cannot ordinarily be x-rayed well even with tomography. Tomography is an x-ray technique whereby the x-ray source and film are moved about during exposure in a fashion so that only one plane through the body or object is clearly seen and other planes are blurred and not distinctly seen. In pneumoencephalography a small amount of air is injected into the spinal column of an erect patient so that is travels up the spinal column and into the ventricles where it displaces some of the cerebral fluid in the ventricles. The difference is sufficient between the x-ray absorption of brain tissue and of air to then make tomographic x-ray exposures showing the shape of the air bubble, which corresponds to the shape of the ventricles bounding the air bubble. Ordinarily a series of many exposures is made during which the patient is positioned in different orientations with respect to gravity so that the air bubble moves around to different ventricles and to different sides of the same ventricles.

Prior art apparatus for carrying out this method includes a patient supporting apparatus that is capable of moving the patient into the many required positions. Once the patient has been properly positioned with respect to gravity and the bubble is theoretically at a desired location, the supporting apparatus and patient are positioned with respect to a tomography machine so that one or more tomograms of the brain can be made with the patient and bubble in that position. Thereafter, the patient is repositioned and the supporting apparatus and patient are again positioned with respect to the tomography machine for more tomograms of the brain. Because the patient's head must be positioned very close to the tomography table and at a fairly precise location, in prior art apparatus, the patient must be moved at least slightly away from the table for repositioning because the table would otherwise interfere with the repositioning. After the patient is repositioned, his head must then again be brought very close to the tomography table and to a fairly precise location. It should be appreciated that at least six, preferably nine, and possibly as many as twelve or more patient positions are required and that each time the head must be accurately positioned with respect to the tomography machine. Prior art supporting apparatus obviously has means for making accurate position adjustment, but the procedure is time consuming and prone to error due to the large number of required accurate positionings.

Pneumoencephalography is a very traumatic and painful experience for the patient, so that repetition of the study is very undesirable. Since the entire procedure is also very time consuming, taking several or more hours, any reduction in time required for the procedure is also very desirable.

BRIEF SUMMARY OF THE INVENTION

It is an object of this invention to provide an isocentric means of positioning a patient for peneumoencephalography studies. It is a further object to make the positioning isocenter correspond to the geometric center of the region under study, namely the ventricles of the brain.

Another object is to provide full positioning freedom about the region under study without moving the region of study out of position for taking tomograms thereof.

A further object is to provide patient supporting and positioning apparatus for pneumoencephalography studies which does not require more than one accurate positioning procedure.

Still another object is to provide patient supporting and positioning apparatus for pneumoencephalography which detachably mounts onto a tiltable tomography table.

These and other objects will be apparent from the detailed description of this invention.

A large annular bearing is detachably mountable onto the top surface of a tiltable tomography table in a position such that the axis of the bearing corresponds to the axis of the central ray of the tomography machine. Attached to and supported by this bearing is a chair adapted to support and restrain a patient with his head positioned close to the table on the axis of the central ray. The bearing permits rotation of the chair about the axis of the bearing, thereby permitting rotation of the patient about his head positioned on this axis. The chair is rotatably supported by a shaft having an axis which also passes through the patient's head and furthermore also intersects the axis of the bearing at a point within the patient's head. The shaft axis is inclined from the surface of the table at an angle of preferably about eleven degrees and the patient fits within a space defined by a cone of preferably about twenty-two degrees centered on this axis. The intersection of the rotation axes or positioning isocenter corresponds with the geometric center of tomographic study and the patient may be accurately positioned so that this isocenter corresponds to the geometric center of the ventricles. Thus, the patient may be rotated about the shaft and about the axis of the bearing without moving the geometric center of the ventricles or any other defined center of study with respect to the table.

BRIEF DESCRIPTION OF THE DRAWINGS

FIG. 3 is a more detailed side view of the chair mounted on a vertically positioned tomography table.

FIG. 5 is a cut away top sectional view of the shin restraint supporting mechanism.

FIG. 8 is a cut away top view of the chair supporting mechanism.

FIG. 9 is a cross sectional view of the worm wheel drive for rotating the chair about its supporting shaft.

FIG. 10 is a detailed view of the lever assembly which releases the chair for rotation about the main bearing.

FIGS. 12 and 13 are top and side view respectively of the assembly for detachably mounting the main bearing to the table.

FIG. 14 is a side cross sectional view of a portion of the main bearing.

FIGS. 15, 16 and 17 are top, front and side cross sectional view of the pin locking assembly for the main bearing.

FIG. 21 illustrates a chair supporting a patient in a position where all degrees of movement freedom have been exercised.

DETAILED DESCRIPTION OF THE PREFERRED EMBODIMENT

Figure 1:
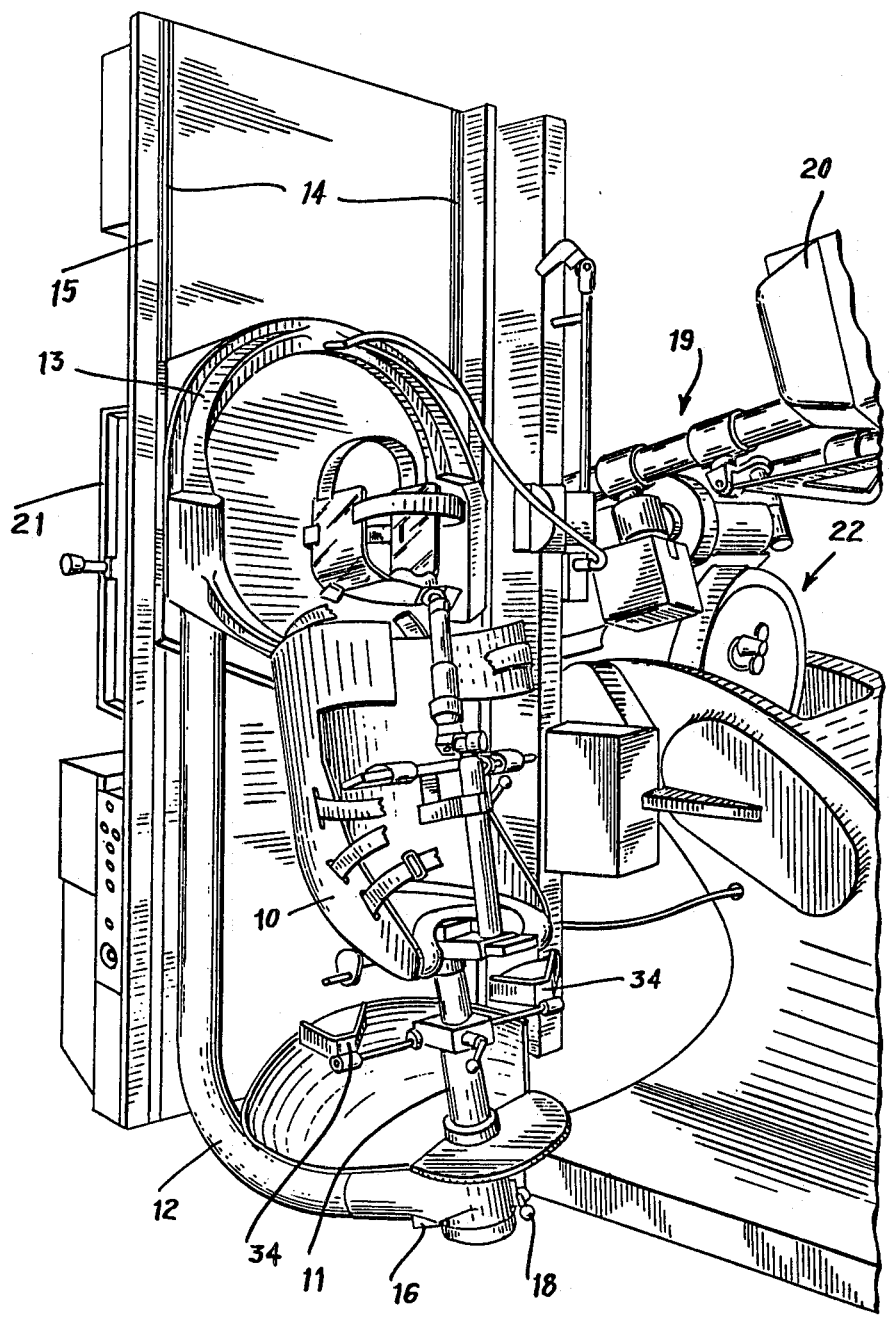
FIG. 1 shows one embodiment of the novel patient supporting chair in perspective mounted on a vertically positioned tomography table.
Figure 2:
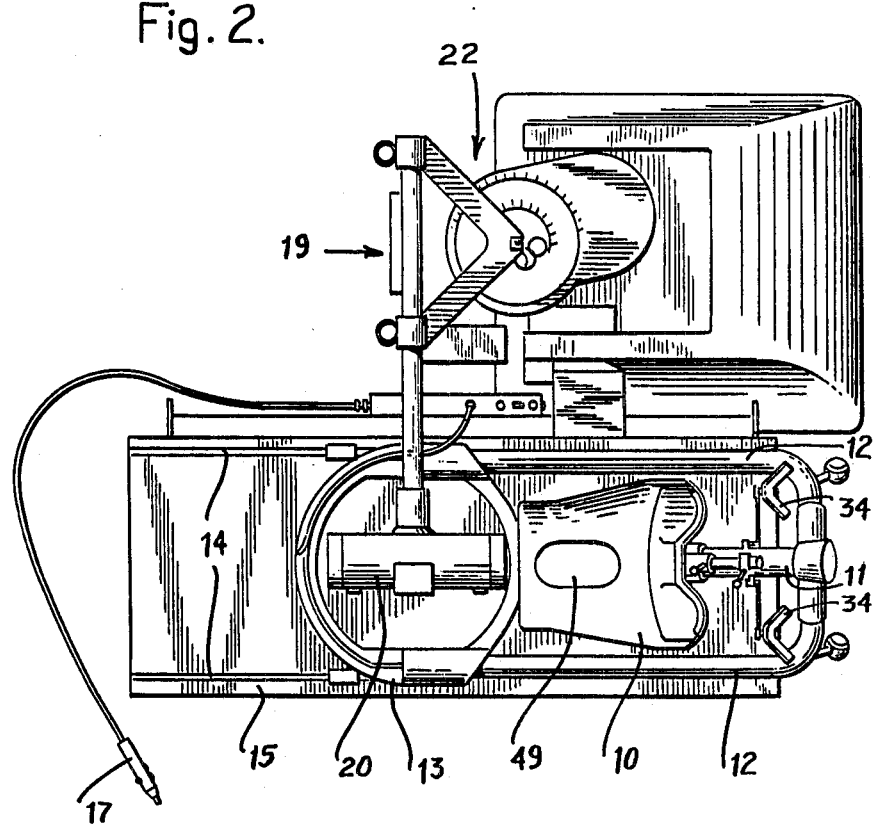
FIG. 2 is a top view of the chair mounted on a tomography table which is a horizontal position.

Referring now to the drawings generally and more specifically to FIGS. 1, 2 and 21, a patient supporting chair 10 is mounted on a main support shaft 11 which is rotatably supported by tubes 12. Main bearing 13 is detachably mounted to rails 14 in tomographic table 15 and supports tubes 12 in cantilever fashion. Motor 16 at the base of shaft 11 rotates shaft 11 and is controlled with hand control 17 (FIG. 2). A lever 18 releases main bearing 13 for rotation. A parallelogram arrangement of mechanical arms 19 associates the motion of x-ray source 20 to the motion of x-ray film holder 21 for making tomograms. The particular blurring trajectory or geometric pattern traced by the source and holder in this embodiment is variable and may be adjusted by means of gearbox apparatus generally indicated by reference numeral 22. Tomographic table 15 may be tilted from horizontal to vertical with hand control 17 and source 20 and film holder 21 rotate with the table so that the orientation thereof does not change with respect to the table.

Tomography apparatus 15, 19-22 is of a type commerically available and in common use. One example of such a machine is the polytome U3 sold by Philips Medical Systems, Inc., Shelton Connecticut. In this device the blurring trajectory may be linear, circular, elliptical or hypocycloidal, with a free choice of orientation thereof. A detailed understanding of such tomography apparatus is not required for a full understanding of the present invention.

Figure 4:
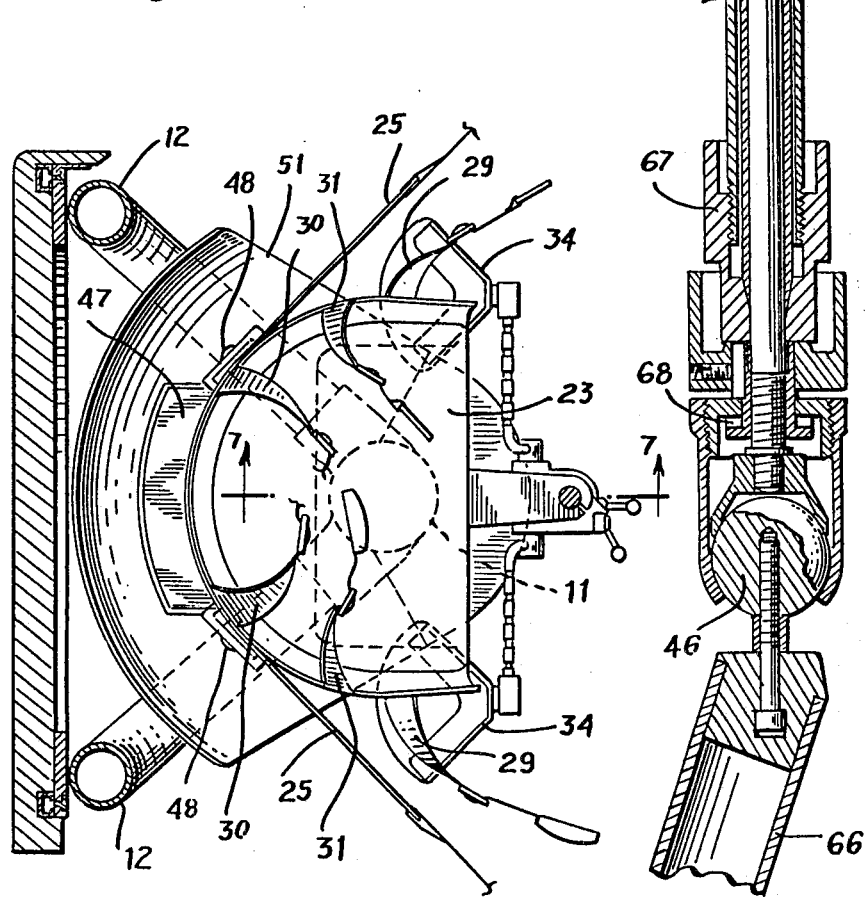
FIG. 4 is a cut away top sectional view of the chair mounted on a vertically positioned table.

Referring now more particularly to FIGS. 3 and 4, the main bearing 13 supports two tubular members 12, which in turn carry the main shaft which supports the chair 10. The chair 10 includes a padded seat 23 with integral back support 24. Shoulder support 25 wraps around the patient and is secured in the front with one or more velcro closure straps. Shoulder support 25 may be adjusted up and down and a semi-flexible band 26 secures it to the back support 24 by engaging a pin 27 with one of several different holes in the band 26. Bar 28 assures by its proximity to pin 27 that pin 27 will remain engaged with any selected hole in band 26. This arrangement functions like some apparel belt buckles. Strap 29 holds the patient's thighs against seat 23. Strap 30 engages the patient's abdomen and forces his lower back against back support 24. Strap 31 crosses the patient's chest and holds the upper back and shoulders against shoulder support 25. There is another strap 31 crossing the chest from the other shoulder.

Mechanically linked rigidly with the chair seat or the shaft supporting the chair seat is a support arm 32 which carries an auxiliary support shaft 33. Shin restraint 34, forearm restraint 35 and head restraint 36 are all supported by arm 32. Head restraint 36 comprises an integrally molded plastic member 37 that resembles a portion of a football helmet. Member 37 supports four straps 38, 39, 40 and 41 which hold the patient's head in a fixed position relative to member 37. Ordinarily, padding is placed for comfort between the head and member 37 and between the head and straps 38, 39 40 and 41. Member 37 may be molded in many forms so long as it functions to hold the head firmly in a fixed position. Head support 36 also includes a chin support 43 and both member 37 and the chin support 43 are supported by shaft 44 which has ball joints 45 and 46 on either end for adjustment freedom. Shaft 44 furthermore is adjustable in length as will be described in further detail below with reference to FIG. 7.

A tray 47 of sterilizable material is detachably mounted to the rear of seat 23 via thumb screws 48 to hold medical supplies and tools during the spinal surgical procedure. An opening 49 (FIG. 2) in the back support 24 of the chair permits access to the lumbar region of the spine where a puncture is made, cerebrospinal fluid removed and small amounts of air injected.

The height of the chair 10 is adjustable by turning crank 50. In FIG. 3 all body support elements except toe guard 51 are mechanically attached to the chair so that adjustment of the height via crank 50 moves all support elements together. It is alternatively possible, though not preferred, to secure certain support elements directly to shaft 11. FIGS. 1, 2 and 21, for example, show an embodiment where the shin supports 34 are mechanically attached to shaft 11 and do not therefore move up or down with the chair 10. Casters 52 are used to roll the entire patient support apparatus to and from the table in wheel barrow fashion.

FIG. 5 shows in cross section the shin restraint supporting mechanism which clamps onto auxiliary support shaft 33. Hand crank 53 is used to rotate shaft 54 which turns screw 55 to reduce spaces 56, thereby frictionally securing the element 57 to shaft 33 and shaft 58 to element 57. Rods 59 are secured to shaft 58 by pins 60. Shin restraints 34 are attached along rods 59 as shown more clearly in FIG. 8. A simple turn of crank 53 thus secures or releases the shin restraints.

Figure 6:
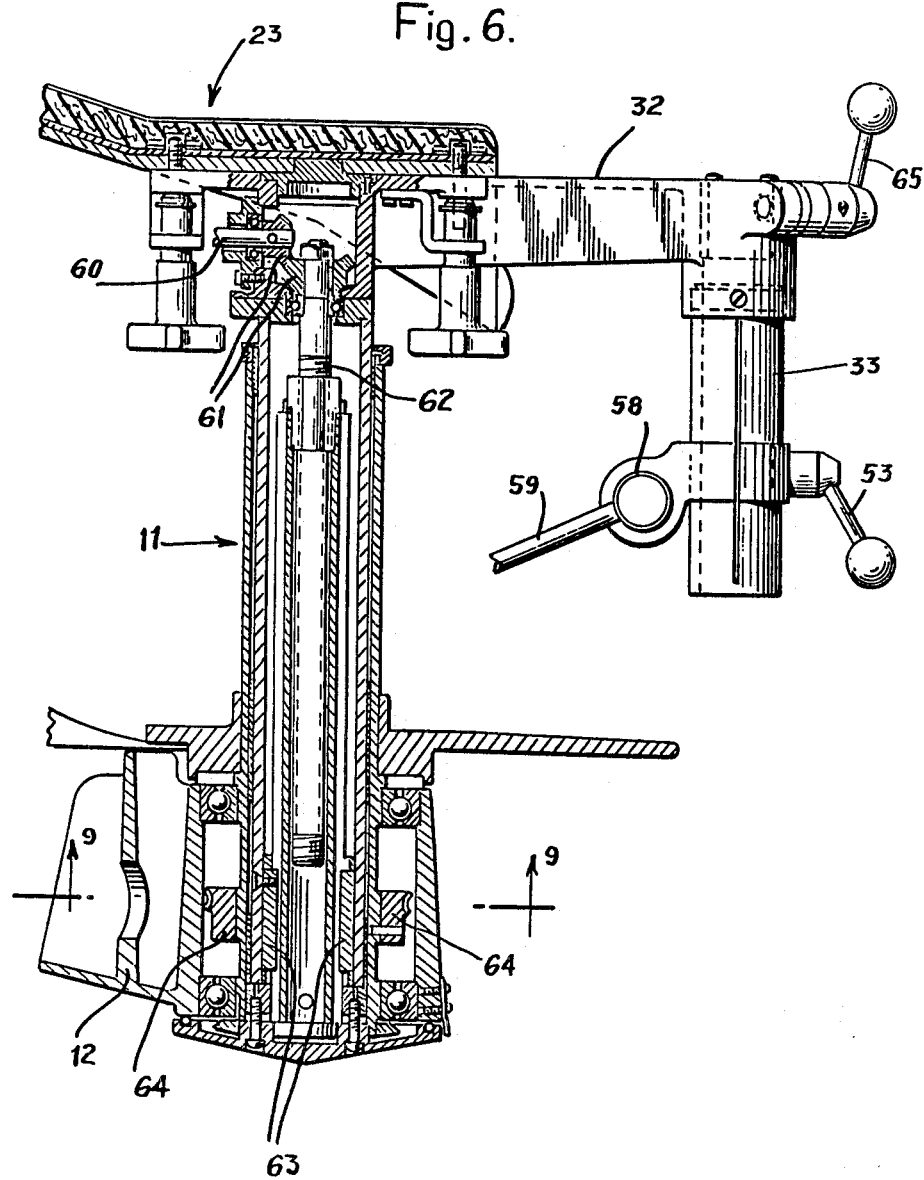
FIG. 6 is a side cross sectional view of the shaft which supports the chair and the main support shaft for the chin, arm and shin restraints.

FIG. 6 is a side view of the main support shaft 11. Crank rod 60 drives bevel gears 61 which rotate jack screw 62 and raises or lowers seat 23. Anti-rotation shoes 63 link rotation of the seat 23 to worm wheel 64, which is driven by a motor as is more clearly shown in FIG. 9. Hand crank 65 operates similarly to previously described crank 53 to clamp thereto the shaft which supports the forearm and head restraints.

Figure 7:
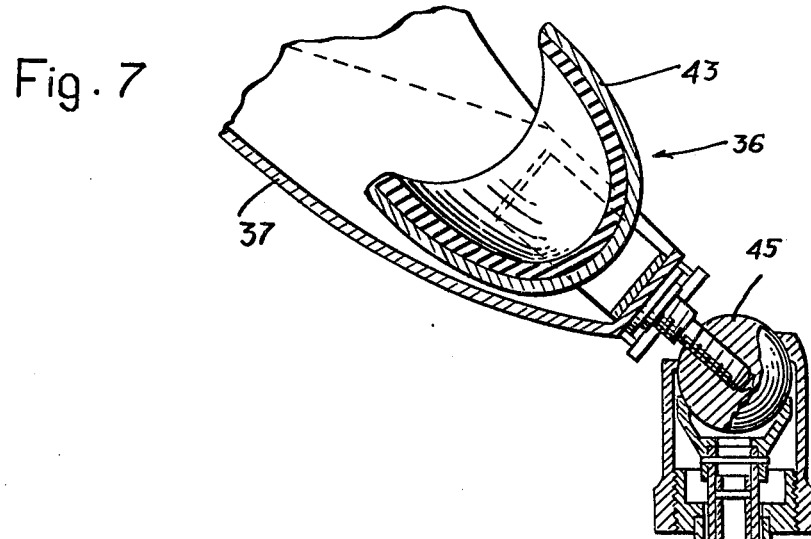
FIG. 7 is a side cross sectional view of the chin restraint.

FIG. 7 is a cross sectional view of shaft 44 which supports the head restraint 36. Shaft 66 is mechanically secured to chair 10 via crank 65 as above described. Lock nut 67 cooperates with thrust bearing 68 to simultaneously lock the positions of ball joints 45 and 46 as well as telescoping shaft 44.

FIG. 8 shows a cut away top view of the chair supporting mechanism. Seat 23 is attached to bracket 69 by four hand screws 70. Bracket 32 supports the shaft 33 which via element 57 and shaft 58 supports shafts 59. Shin restraints 34 are mounted on shafts 59 at any one of several different regions of reduced diameter by spring loaded pins 71. Pins 71 have a region of greater diameter for engagement with the regions of reduced diameter on shaft 59. Crank rod 60 is turned by crank handle 72 to raise or lower the seat 11 as previously described. An additional crank rod 73 and handle 74 serve the same purpose and facilitate hand adjustment of height from the opposite side.

FIG. 9 illustrates the worm wheel drive for the main shaft 11. Motor 16 turns worm wheel 64 which turns the main shaft assembly concentric therewith. Cable 77 controls motor 16 and is carried inside one of the tubes 12 to bearing 13. Lever 18 pulls bowden wire 76 to release the main bearing 13.

FIG. 10 is a more detailed view of the lever assembly connecting lever 18 to bowden wire 76. Cranking handle 18 turns shaft 78 and swings arm 79 which is pinned thereto. Bowden wire 76 is attached to arm 79 so as to be pushed or pulled by arm 79.

Figure 11:
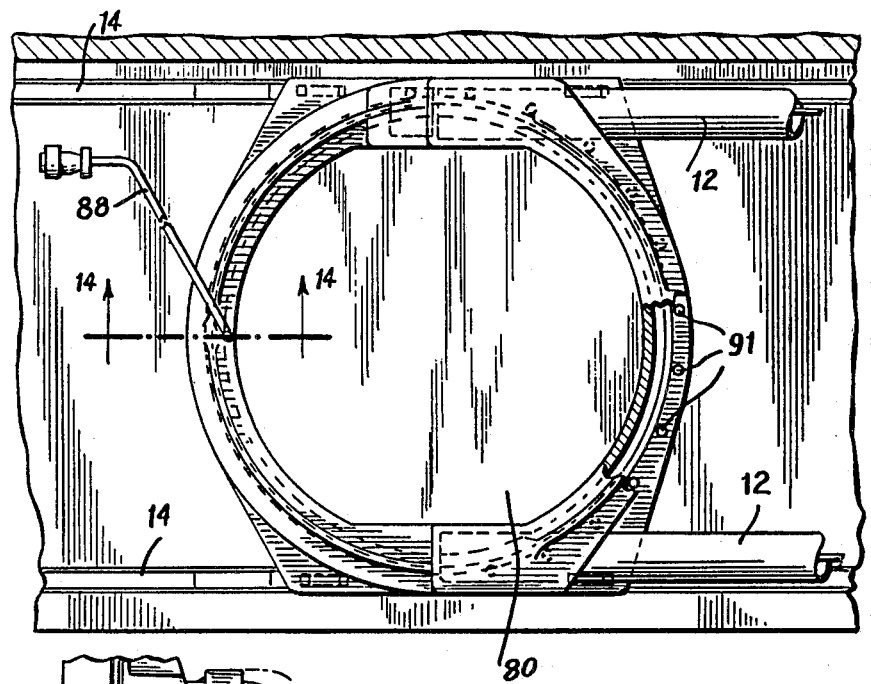
FIG. 11 is a top view of the main bearing.
Figure 20:
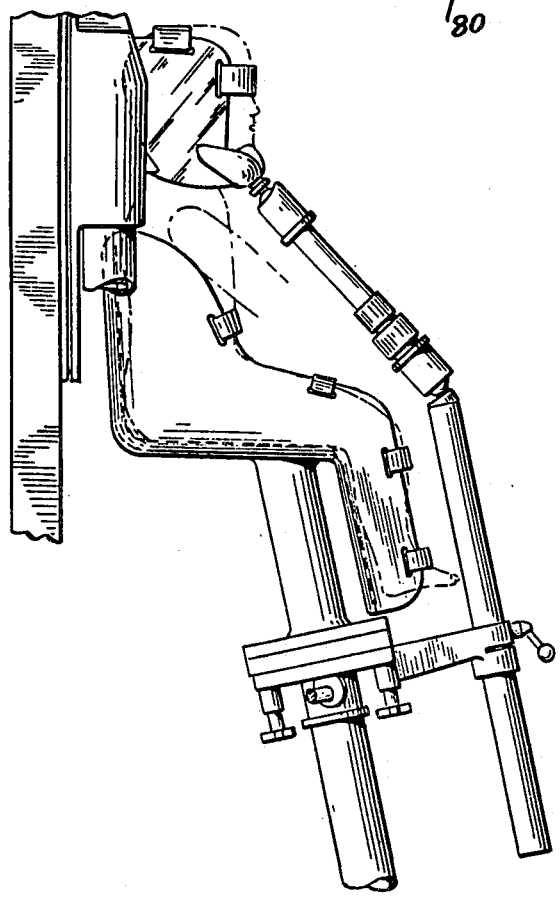
FIG. 20 illustrates a child's chair which may be mounted on the chair supporting shaft in place of the larger chair for adults.

FIG. 11 is a top view and FIG. 14 is a cross-sectional view of the main bearing 13. The large open aperture 80 is substantially larger than a patient's head so that the metal of the bearing does not interfere with tomography within the aperture. A first bearing portion 87 is detachably mounted to the table 15 via rails 14. Bearing portion 81 is annular with an inward flange portion 82. A second bearing portion 83 which is also annular is rotatably mounted inside of portion 81 and rides on the flange portion 82 via rollers spaced along the flange portion 82. Portion 83 comprises a top annular element 85 and a bottom annular element 86 attached together with screws 87. Cable 88 contains electrical wires for powering motor 16 and for sensing the condition of a microswitch 89 (FIG. 15). A hollow channel 90 in bearing 13 carries electrical wires from cable 88 to microswitch 89 and to the tube 12 which leads to motor 16. Spaced at about 15 degree intervals around half of the circumference of bearing portion 81 are holes 91, the bearing portions 81 and 83 are locked in a predetermined position. In order to rotate bearing portion 83, the pin 92 must be withdrawn from engagement with all of the holes 91 by actuation of lever 18 (FIG. 9) and bowden wire 76. When bowden wire 76 is withdrawn toward lever 18, microswitch 89 is triggered to cause a visual indication of the pin release. Withdrawl of the bowden wire 76 rotates member 93 about axis 94 to lift pin 92 against spring 95 (FIGS. 15, 16 and 17).

Main bearing 13 may be held to rails 14 in any convenient manner. A preferred method employs a member 96 (FIGS. 12 and 13) which fits into rails 14 from the ends thereof and cannot be pulled out perpendicular to the table. Element 96 has two slots 97 and 98 which receive flange portions 99, 100, 101, 102 attached rigidly to bearing 13. Portions 99, 100, 101, 102 fit directly into slots 97, 98 from the table top and may be lifted away with bearing 13 when lever 103 is in the position shown in FIG. 13. However, when lever 103 is depressed, portions 102 and 103 are forced apart and the inclined sides of portions 96, 100, 101 and 103 contact each other forcing element 96 against the top inside surface of rails 14. A strong frictional attachment is thereby formed between bearing 13 and rails 14 via element 96. Lever 103 has a pivot 104 sufficiently low to assure that it passes center position so that the lever stays depressed until manually raised. Arm 105 is adjustable so that portions 99 and 102 are properly spaced to achieve the above aims. A spring loaded pin 106 fits in hole 107 to accurately locate the locking mechanism with respect to the central ray axis of the tomography apparatus.

Although a thorough understanding of tomography is not required to understand the present invention, an appreciation is required of the location and orientation of the central ray axis and the plane or possible different planes which may be sharply imaged by the tomographic apparatus.

Even when several different geometric patterns may be alternatively selected, each has a geometric center and normally all the geometric centers are in the same position. The axis of the x-ray beam, when it is at this geometric center, may be defined as the axis of the central ray. Alternatively it may be defined as the most central or average of the many orientations that the x-ray beam goes through during a tomography exposure. Whatever the definition, tomography apparatus typically has focal distance adjustments which allow various parallel planes to be sharply imaged. Each such plane has a useful field and each field has a center. A straight line connecting the centers of all the different useful fields is the axis of interest and is herein referred to as the central ray axis or axis of the central ray. In the apparatus illustrated in this embodiment, the central ray axis 108 (FIG. 3) is in a fixed position perpendicular to the table regardless of table tilt, and the parallel planes which may be sharply imaged are all parallel to the table and spaced from the table by distances ranging from zero to 25 cm or about zero to ten inches.

Figure 18:
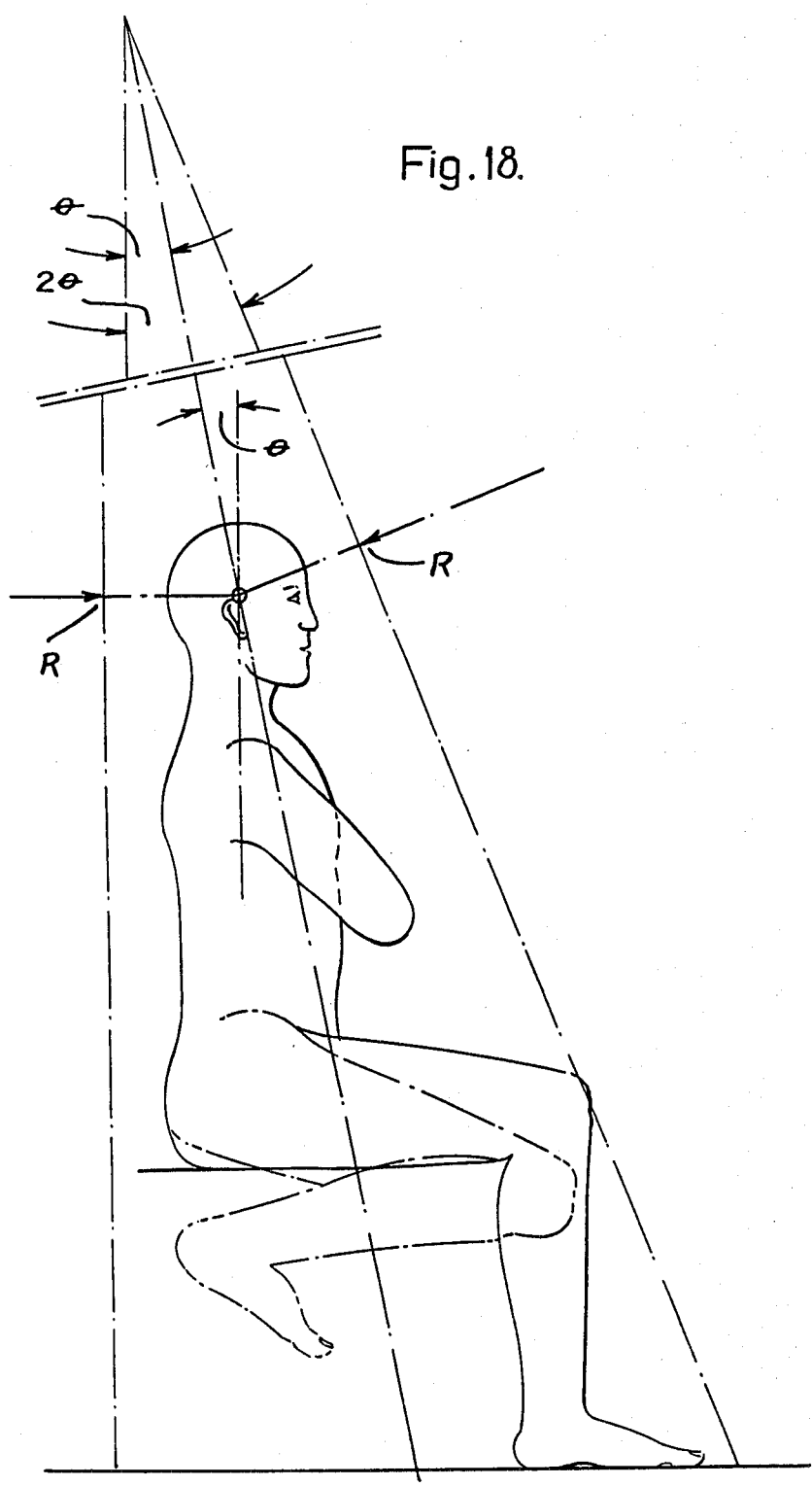
FIGS. 18 and 19 show side and front views respectively of the patient with respect to the axes of rotation and the cone space within which the patient fits.
Figure 19:
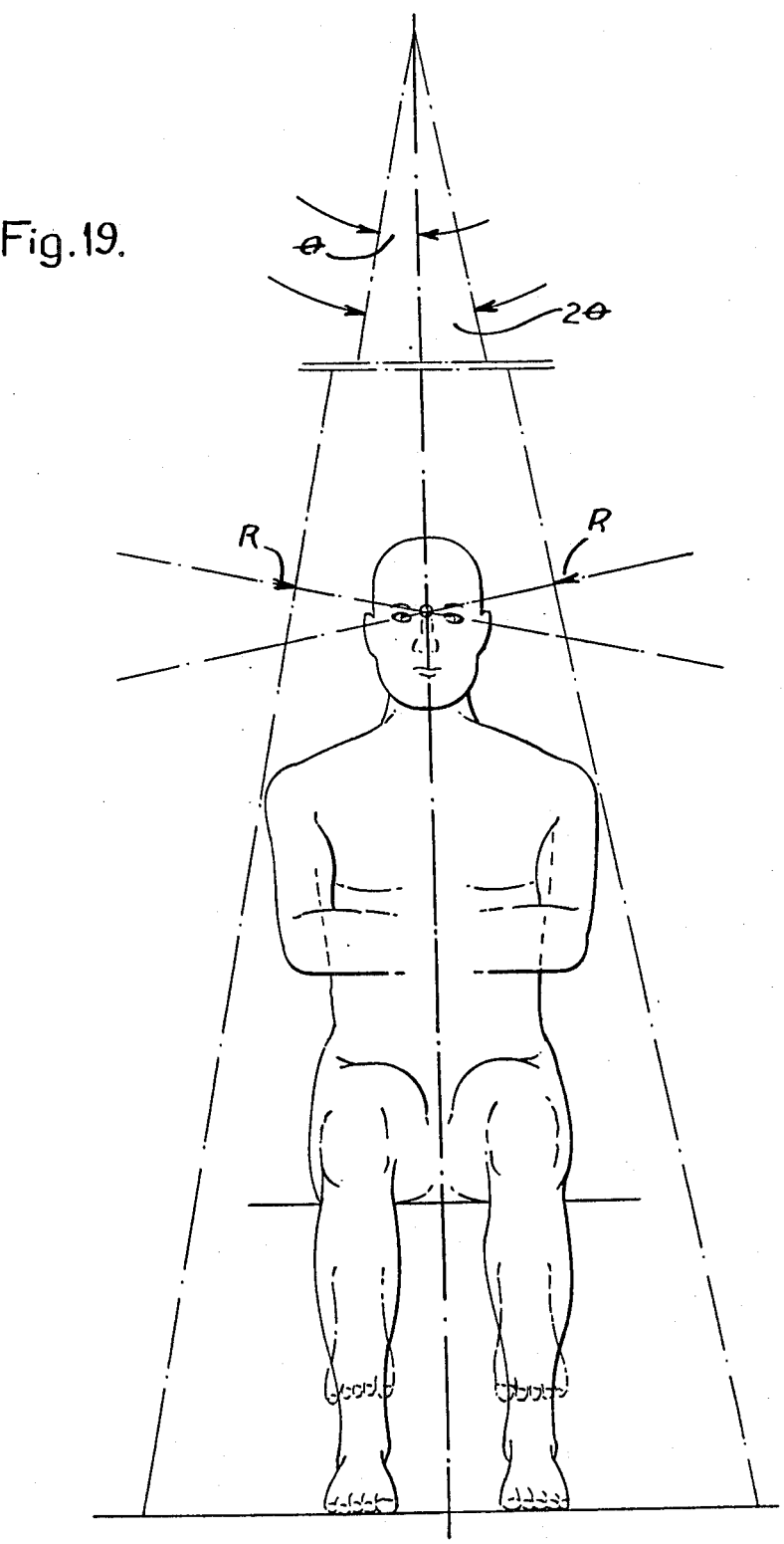

The function of the patient support apparatus herein described is to support the patient and his head so that a defined point within the head remains stationary even though the chair is rotated about the main shaft 11 or about the axis of rotation of bearing 13. It has been determined that at least 99 percent of the adult population may be fitted within the cone region shown in FIGS. 18 and 19, where R is about eight inches and $\theta$ is eleven degrees. The preferred chair is adapted to receive the patient within such a space. The distance to the table from the isocenter is then about eight inches which falls within the range of zero to ten inches and still permits slices to be taken up to two inches above the defined isocenter. The isocenter is preferably located at some point between three cm anterior to the middle ear and three cm posterior to the middle ear and in the lateral direction between the mid-orbits.

What is claimed is:

1. X-ray diagnostic apparatus, comprising an image recording device positioned to intercept X-rays from an X-ray source, a tiltable patient table in the path of X-rays between the image recording device and the X-ray source, a frame mounted on and rotatable with respect to the table, a patient support in said frame, said frame being rotatable with respect to the stationary table about a first axis extending perpendicularly to the plane of the table in a plane parallel to the plane of the table, the patient support being rotatable with respect to the frame about a second axis which intersects the first axis in an isocentre situated above the plane of the table, said second axis enclosing an acute angle with the plane of the table, a central ray of said X-ray source extending through the isocentre for all mutual positions of X-ray source, frame and patient support.

2. An apparatus as claimed in claim 1, wherein the frame comprises two parallel supporting arms which are secured adjacent one end in diametrically oppositely situated points of an annular bearing which is mounted on the table, the other ends of said supporting arms supporting a telescopic column on which the patient support is mounted, the axis of said column coinciding with said second axis which intersects said first axis in the isocentre.

3. An apparatus for X-ray diagnosis as claimed in claim 1, wherein the X-ray source and the image recording device are mounted in a rod-like parallelogram which is rotatable about a tomographic axis which is parallel to the plane of the table and which extends through the isocentre, said axis being situated between the X-ray source and the image recording device, the tomographic axis being parallel to the plane of the rod-like parallelogram, said rod-like parallelogram also being rotatable about a further axis which is perpendicular to the plane of the rod-like parallelogram and the tomographic axis.

* * * * *